US010918397B2

(12) United States Patent
Courtney, Jr. et al.

(10) Patent No.: US 10,918,397 B2
(45) Date of Patent: Feb. 16, 2021

(54) DEVICE FOR MAINTAINING ALIGNMENT OF A CANNULATED SHAFT OVER A GUIDE PIN

(71) Applicant: Tornier, Inc., Bloomington, MN (US)

(72) Inventors: Robert Courtney, Jr., Pierceton, IN (US); Brian C. Hodorek, Winona Lake, IN (US); Matthew J. Purdy, Leesburger, IN (US)

(73) Assignee: Tornier, Inc., Bloomington, MN (US)

( * ) Notice: Subject to any disclaimer, the term of this patent is extended or adjusted under 35 U.S.C. 154(b) by 225 days.

(21) Appl. No.: 16/059,569

(22) Filed: Aug. 9, 2018

(65) Prior Publication Data

US 2018/0344331 A1    Dec. 6, 2018

Related U.S. Application Data

(62) Division of application No. 14/670,065, filed on Mar. 26, 2015, now Pat. No. 10,070,873.
(Continued)

(51) Int. Cl.
*A61B 17/17*       (2006.01)
*A61B 17/16*       (2006.01)
(Continued)

(52) U.S. Cl.
CPC .......... *A61B 17/17* (2013.01); *A61B 17/1624* (2013.01); *A61B 17/1628* (2013.01);
(Continued)

(58) Field of Classification Search
CPC . A61B 17/17; A61B 17/1717; A61B 17/1721; A61B 17/1725; A61B 17/1732;
(Continued)

(56) References Cited

U.S. PATENT DOCUMENTS 2,243,717 A     11/1938   Godoy
4,055,185 A  *  10/1977   Waldron ............ A61B 17/1633
                                                        606/180
(Continued)

FOREIGN PATENT DOCUMENTS

EP          0546769        6/1993
EP          0880340 B1    10/2003
(Continued)

OTHER PUBLICATIONS

Extended European Search Report issued in European Patent Application No. 15161457.5, dated Dec. 3, 2015.

*Primary Examiner* — Amy R Sipp
(74) *Attorney, Agent, or Firm* — Knobbe, Martens, Olson & Bear, LLP

(57) ABSTRACT

An orthopedic driver is provided that includes an elongate tubular body and an indicator assembly. The indicator assembly has a housing that has at least one opening and a visual indicator disposed in the at least one opening. The visual indicator is configured to be coupled with a guide pin such that lateral movement of the elongate tubular body relative to the guide pin causes the visual indicator to move between a flush or recessed configuration within the housing and an extended configuration. In the extended configuration, the visual indicator extends outward of an outer surface of the housing. The flush or recessed configuration corresponds to alignment of the guide pin relative to the elongate tubular body and the extended configuration corresponds to misalignment of the guide pin relative to the elongate tubular body.

18 Claims, 11 Drawing Sheets

Related U.S. Application Data

(60) Provisional application No. 62/018,963, filed on Jun. 30, 2014.

(51) Int. Cl.
*A61B 17/00* (2006.01)
*A61B 17/68* (2006.01)

(52) U.S. Cl.
CPC ...... *A61B 17/1631* (2013.01); *A61B 17/1633* (2013.01); *A61B 17/1684* (2013.01); *A61B 17/1778* (2016.11); *A61B 2017/00119* (2013.01); *A61B 2017/681* (2013.01)

(58) Field of Classification Search
CPC ............ A61B 17/1735; A61B 17/1746; A61B 17/1778; A61B 17/1624; A61B 17/1631; A61B 17/1684; A61B 17/1666; A61B 17/1633
USPC ........... 606/104; 33/511, 512, 645, 520, 638
See application file for complete search history.

(56) References Cited

U.S. PATENT DOCUMENTS

| | | | |
|---|---|---|---|
| 4,534,114 A * | 8/1985 | Woyton | G01B 5/25 |
| | | | 33/645 |
| 5,429,641 A * | 7/1995 | Gotfried | A61B 17/1721 |
| | | | 411/383 |
| 5,452,521 A * | 9/1995 | Niewmierzycki | H01L 21/68 |
| | | | 33/520 |
| 6,102,915 A | 8/2000 | Bresler et al. | |
| 6,402,757 B1 | 6/2002 | Moore, III et al. | |
| 6,623,488 B1 | 9/2003 | Leone, Jr. | |
| 6,743,235 B2 | 6/2004 | Rao | |
| 6,827,722 B1 * | 12/2004 | Schoenefeld | A61B 17/1622 |
| | | | 606/104 |
| 7,666,189 B2 | 2/2010 | Gerber et al. | |
| 7,771,429 B2 | 8/2010 | Ballard et al. | |
| 8,167,823 B2 | 5/2012 | Nyez et al. | |
| 8,257,409 B2 | 9/2012 | Schlienger et al. | |
| 8,454,619 B1 | 6/2013 | Head | |
| 8,469,962 B1 | 6/2013 | Head | |
| 8,641,717 B2 * | 2/2014 | Defossez | A61B 17/8872 |
| | | | 606/86 R |
| 8,888,786 B2 | 11/2014 | Stone et al. | |
| 8,974,468 B2 | 3/2015 | Borja | |
| 9,138,258 B2 | 9/2015 | Geebelen | |
| 2002/0016599 A1 | 2/2002 | Thomas, III et al. | |
| 2002/0123668 A1 | 9/2002 | Ritland | |
| 2004/0138667 A1 * | 7/2004 | Kimura | A61B 17/1622 |
| | | | 606/80 |
| 2005/0059975 A1 * | 3/2005 | Fanger | A61B 17/1671 |
| | | | 606/80 |
| 2006/0106399 A1 | 5/2006 | Taras et al. | |
| 2007/0005074 A1 | 1/2007 | Chudik | |
| 2007/0027417 A1 | 2/2007 | Chudik | |
| 2007/0156126 A1 | 7/2007 | Flaherty | |
| 2007/0162046 A1 * | 7/2007 | Vandewalle | A61B 17/8875 |
| | | | 606/108 |
| 2007/0233141 A1 | 10/2007 | Park et al. | |
| 2007/0233150 A1 * | 10/2007 | Blain | A61B 17/1757 |
| | | | 606/96 |
| 2007/0282345 A1 | 12/2007 | Yedlicka et al. | |
| 2009/0187194 A1 | 7/2009 | Hamada | |
| 2010/0179560 A1 * | 7/2010 | Chenaux | A61B 17/8875 |
| | | | 606/104 |
| 2010/0228253 A1 * | 9/2010 | Plecko | A61B 17/1637 |
| | | | 606/80 |
| 2011/0034775 A1 | 2/2011 | Lozman et al. | |
| 2011/0130760 A1 | 6/2011 | Anderson et al. | |
| 2011/0213371 A1 * | 9/2011 | Anthony | A61B 17/1666 |
| | | | 606/85 |
| 2011/0251597 A1 * | 10/2011 | Bharadwaj | A61B 17/1757 |
| | | | 606/1 |
| 2012/0123419 A1 * | 5/2012 | Purdy | A61B 17/1615 |
| | | | 606/83 |
| 2012/0130279 A1 | 5/2012 | Stone | |
| 2012/0130375 A1 * | 5/2012 | Gillard | A61B 17/1617 |
| | | | 606/80 |
| 2012/0226283 A1 | 9/2012 | Meridew et al. | |
| 2013/0012945 A1 | 1/2013 | Chreene et al. | |
| 2013/0053856 A1 | 2/2013 | Penenberg | |
| 2013/0053858 A1 | 2/2013 | Penenberg | |
| 2013/0053904 A1 | 2/2013 | Penenberg | |
| 2013/0211408 A1 | 8/2013 | Kather et al. | |
| 2014/0012389 A1 | 1/2014 | Ek | |
| 2014/0107651 A1 | 4/2014 | Meridew et al. | |
| 2014/0171946 A1 * | 6/2014 | Benson | A61B 17/17 |
| | | | 606/79 |
| 2014/0276892 A1 * | 9/2014 | Pakzaban | A61B 17/8875 |
| | | | 606/104 |
| 2015/0073424 A1 | 3/2015 | Couture et al. | |
| 2015/0374387 A1 | 12/2015 | Courtney, Jr. et al. | |

FOREIGN PATENT DOCUMENTS

| | | |
|---|---|---|
| EP | 1416864 B1 | 2/2008 |
| EP | 1639950 B1 | 6/2009 |
| EP | 1474047 B1 | 11/2010 |
| EP | 1651151 B1 | 6/2012 |
| EP | 2491873 B1 | 5/2015 |
| EP | 2708194 B1 | 5/2015 |
| EP | 1434525 B1 | 7/2015 |
| WO | WO 2012/024271 | 2/2012 |
| WO | WO 2013/022876 | 2/2013 |
| WO | WO 2014/147529 | 9/2014 |

* cited by examiner

DEVICE FOR MAINTAINING ALIGNMENT OF A CANNULATED SHAFT OVER A GUIDE PIN

INCORPORATION BY REFERENCE TO ANY PRIORITY APPLICATIONS

This application is a divisional of U.S. patent application Ser. No. 14/670,065, filed Mar. 26, 2015, which claims the benefit of U.S. Provisional Patent Application Ser. No. 62/018,963, filed on Jun. 30, 2014, which is incorporated by reference herein in its entirety for all purposes. Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

This application relates to apparatuses and methods for maintaining alignment of cannulated shafts over slender guide structures, such as guide pins.

Description of the Related Art

It is conventional in orthopedics to use a drill or other driver tool equipped with a drill bit to modify bone and to deliver implants into a bone surface or cavity. A surgeon can use a simple technique to guide the advancement of the drill bit, such as simply visually confirming that the drill bit is advancing in a proper direction relative to the bone surface or cavity. Such simple techniques are adequate for gross alignment of the direction of advance of a drill bit but are inadequate where higher precision is desired.

A technique for improving guidance of a drill bit is to first place a rigid guide pin into the bone. In this technique, the drill bit has a hollow shaft that is placed over the guide pin. As a result, the inner surface of the shaft and the outer surface of the guide pin interact to reduce the range of directions of advance of the hollow shaft of the drill bit relative to the central longitudinal axis of the guide pin. While a guide pin can reduce the variability of the direction of advance of a drill bit relative to the bone, there is still the possibility that the shaft of the drill bit can be non-parallel to, or otherwise offset from, the guide pin. Also, the guide pin outside of the bone can be bent at an angle relative to the guide pin inserted in the bone thereby not guiding the drill bit along the originally intended direction of the guide pin. A further technique that can be used to correct for such misalignment involves the user re-positioning the drill bit in response to drag between the drill bit shaft and the guide pin. Greater drag indicates a larger angle between the pin and the drill bit shaft. This approach is user and experience dependent, and thus not very reliable or precise.

Complex systems exist for determining an angle of advance of a drill bit by sensing position in space. Such systems require electronics and software which increase the complexity and cost of the system and of procedures utilizing the systems.

SUMMARY OF THE INVENTION

There is a need for new apparatuses and methods for maintaining alignment between a guide pin and a hollow shaft of a drill bit or other tool for driving an implement or implant. Such apparatuses and methods preferably provide one or more immediately visible, audible, and/or vibratory indications of such structures being non-parallel or otherwise off-set or out of alignment. When using a drill or other driver equipped with a drill bit over a guide pin it is desirable to have continuous, real-time feedback that is easy to see, hear and/or feel so that a rotating shaft can be quickly repositioned relative to the guide pin. Thus, the direction of advance of the drill bit can be maintained on or substantially on, e.g., within about a few degrees of, the intended axis of advance. The axis of advance can correspond to the central longitudinal axis of the guide pin.

In one embodiment, an orthopedic driver system is provided that includes a guide pin and a tool assembly. The tool assembly includes an elongate tubular body and an indicator assembly. The elongate tubular body has a distal portion, a proximal portion, and a lumen extending therethrough. The indicator assembly is disposed between the proximal portion and the distal portion of the elongate body. The indicator assembly has a housing that has a plurality of lateral openings. The indicator assembly also has an indicator comprising a plurality of radially extending arms. Each of the plurality of radially extending arms has an outer end slidably disposed in a corresponding lateral opening of the housing. An inner portion of each of the arms is coupled with an inner portion of the indicator. The inner portion of the indicator is configured to be disposed about and in close contact with a side surface of the guide pin. The indicator is rotatable with the elongate tubular body about the guide pin. The indicator is supported in the housing such that a change in the lateral position of the elongate tubular body relative to the guide pin, e.g., adjacent to the indicator, causes the outer end of at least one of the radially extending arms of the indicator to move to a position laterally outward of a lateral surface of the housing.

In one variation of the system, a drill is included. The drill is configured to engage and to rotate the proximal portion of the elongate tubular body.

In another embodiment, an orthopedic driver is provided that includes an elongate tubular body and an indicator assembly. The elongate tubular body has a lumen extending from a distal end to a proximal end. The indicator assembly is disposed between the proximal end and the distal end of the elongate body. The indicator assembly has a housing that has at least one opening and a visual indicator disposed in the at least one opening. The visual indicator is configured to be coupled with a guide pin such that lateral movement of the elongate tubular body relative to the guide pin causes the visual indicator to move between a flush or recessed configuration within the housing and an extended configuration. In the extended configuration, the visual indicator extends outward of an outer surface of the housing. The flush or recessed configuration corresponds to alignment of the guide pin relative to the elongate tubular body and the extended configuration corresponds to misalignment of the guide pin relative to the elongate tubular body.

In another embodiment, an orthopedic driver is provided that includes an elongate tubular body and an indicator assembly. The elongate tubular body has a lumen extending proximally from a distal end thereof. The indicator assembly is disposed proximally of the distal end of the elongate tubular body. The indicator assembly has housing that has a non-smooth surface disposed about an interior lumen thereof. In the orthopedic driver, direct contact is provided between the non-smooth surface and a side surface of the guide pin upon misalignment of the guide pin and the elongate body. The direct contact produces at least one of an audible sound and a vibration during rotation of the elongate tubular body about the guide pin.

In another embodiment, a method is provided in which a distal portion of a guide pin is placed in a bone. An elongate tubular driver is positioned over a proximal portion of the guide pin. The elongate tubular driver has a body that has a mechanical alignment indicator disposed therein. The mechanical alignment indicator is activated upon misalignment of the elongate tubular driver and guide pin. The elongate tubular driver is repositioned in response to at least one of an extension of the mechanical alignment indicator from a side surface of the elongate tubular driver, an emission of an audible sound, and a vibration in the elongate tubular driver. The audible sound and the vibration, if present, arise from direct contact between the mechanical alignment indicator and the guide pin.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of each of the drawings.

FIG. 2A is a transverse cross-sectional view illustrating one form of a mechanical alignment indicator taken at section plane 2A-2A in FIG. 2;

FIG. 2B is a perspective view of a tissue protector having a sleeve with a circumferential gap;

DETAILED DESCRIPTION OF THE PREFERRED EMBODIMENT

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Figure 1:
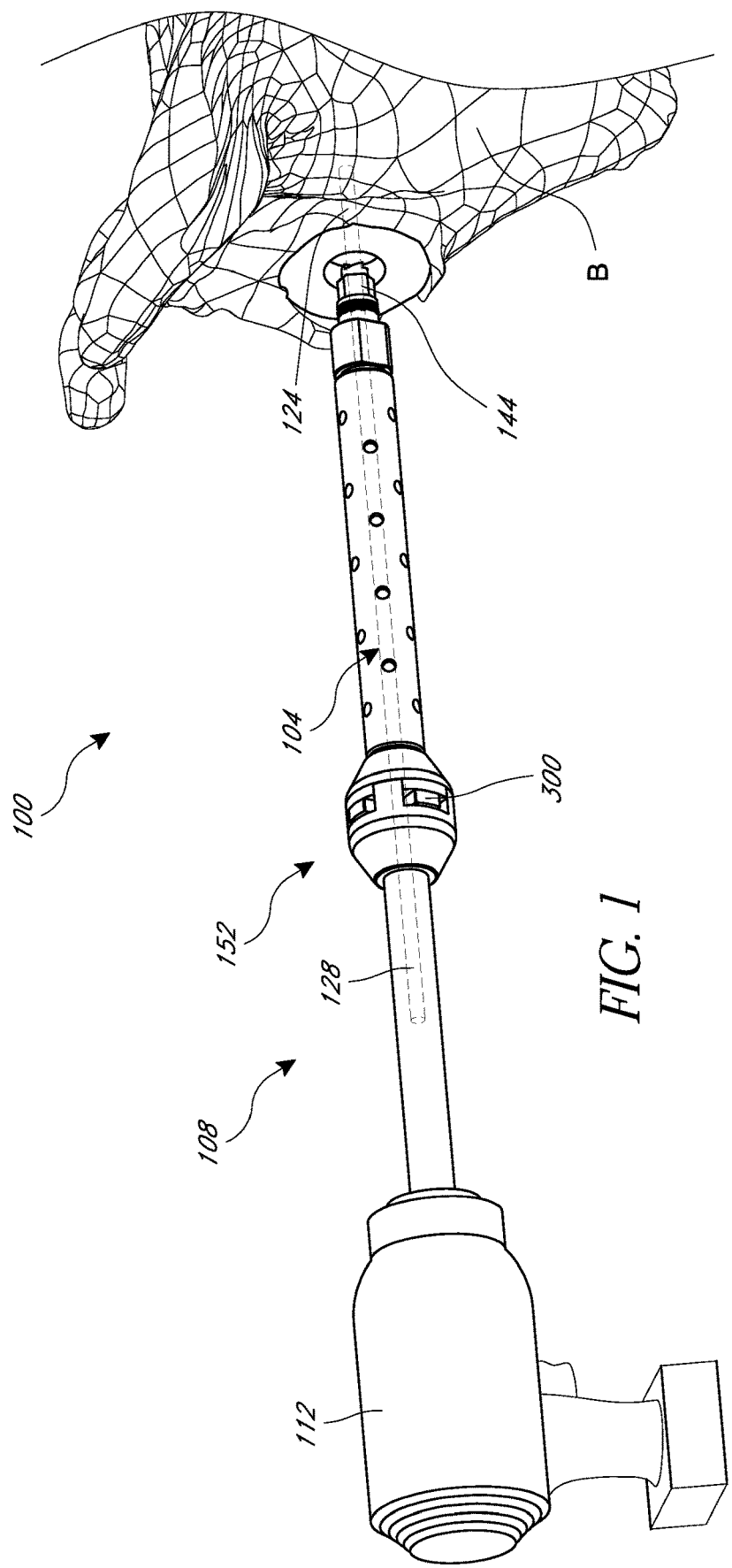
FIG. 1 shows a schematic partial phantom view of an orthopedic driver system being applied to a bone surface.

FIG. 1 shows an orthopedic driver system 100 that includes a guide pin 104, a tool assembly 108, and a drill 112. In the illustration, a distal portion of the system 100 is disposed in the bone B and a proximal portion is coupled with the drill 112. The bone B can be a portion of a shoulder, for example a portion of a scapula.

The guide pin 104 includes a distal end 124, a proximal end 128, and elongate body 132 extending therebetween. FIG. 1 shows that, in use, the distal end 124 is disposed in the bone B. The distal end 124 may be inserted into the bone B to a depth sufficient to retain the pin 104 in the bone B. The proximal end 128 is disposed away from the bone B and is able to receive a cannulated portion of the tool assembly 108. In certain embodiments, the cannulated portion of the tool assembly 108 is longer than the pin 104 such that the proximal end 128 of the pin 104 is disposed inside the tool assembly 108 during operation of the system 100. The guide pin 104 is sufficiently rigid so that it can serve the role of guiding other portions of the driver system 100. The guide pin 104 can be formed of or include a suitable biocompatible metal, such as stainless steel.

Figure 2:
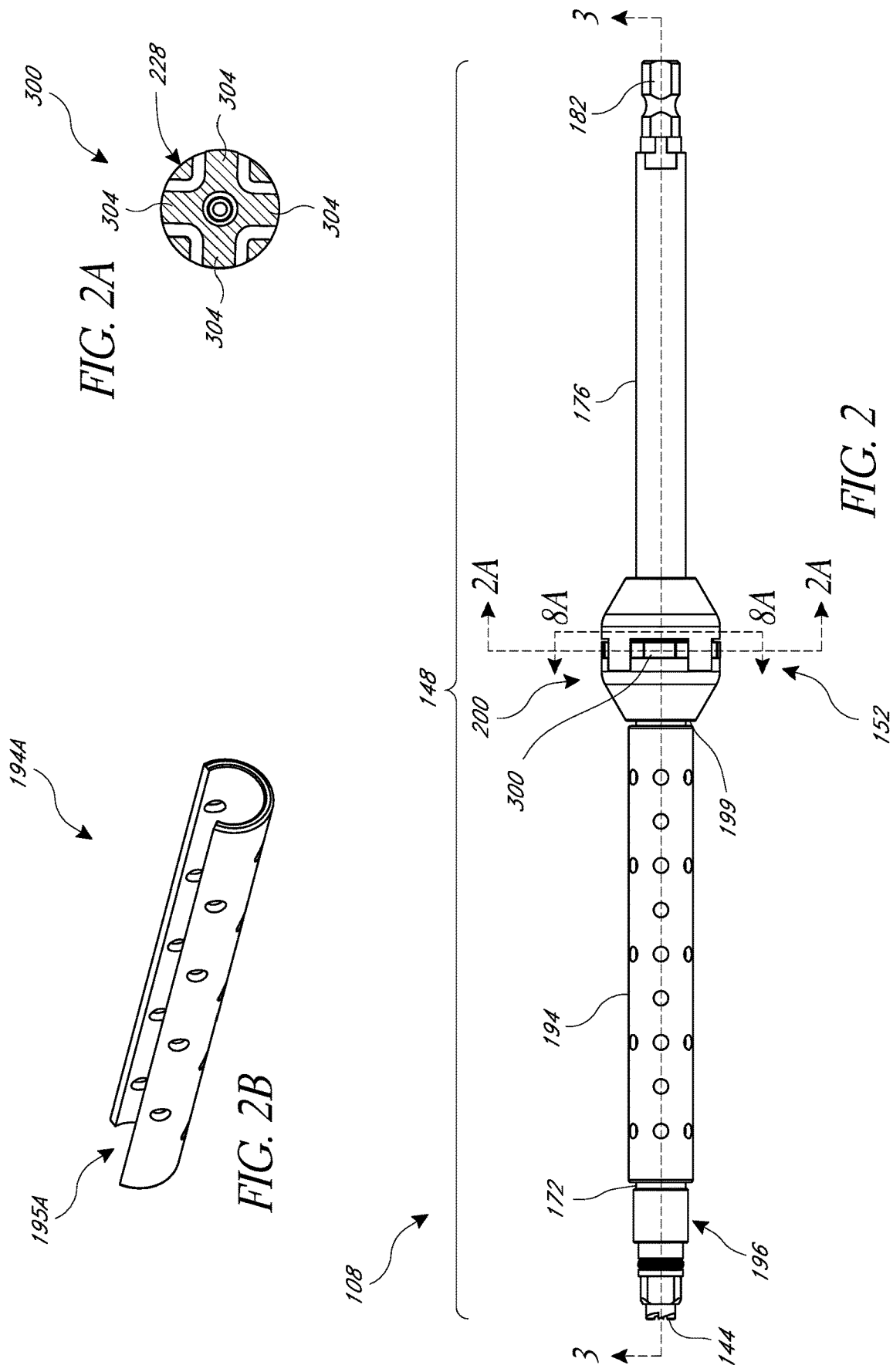
FIG. 2 shows a plan view of an orthopedic driver according to one embodiment.
Figure 3:
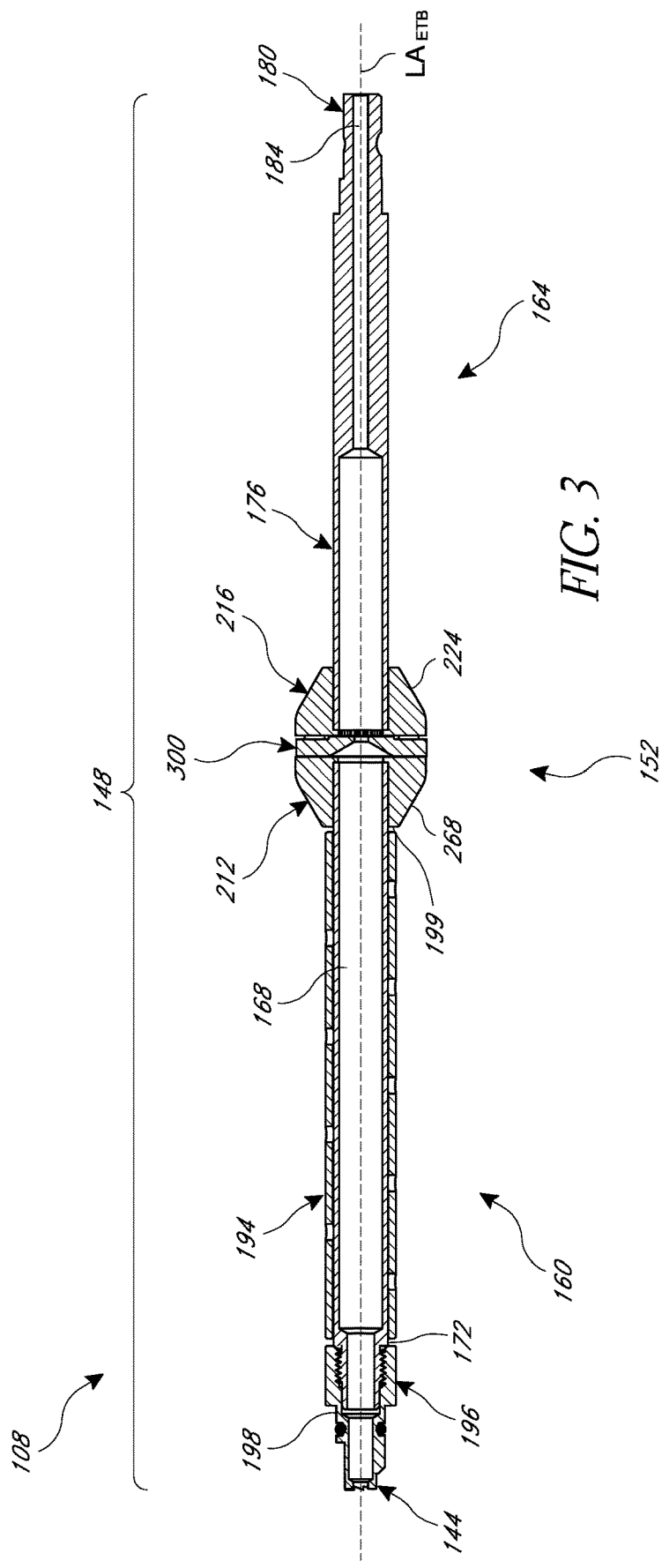
FIG. 3 is longitudinal cross-sectional view of the orthopedic driver of FIG. 2 taken at second plane 3-3.

FIGS. 2 and 3 show the tool assembly 108 in more detail. The tool assembly 108 can be used as an orthopedic driver to transmit a torque from the drill 112 to an implement 144 (discussed further below). The tool assembly 108 includes an elongate tubular body 148 and an indicator assembly 152. In one embodiment the indicator assembly 152 is disposed in a middle section of the elongate tubular body 148. The position of the indicator assembly 152 and the length of the guide pin 104 are such that the proximal end 128 of the guide pin 104 is proximal of the indicator assembly 152 when the implement 144 is at the level of the bone B as shown in FIG. 1. The implement 144 can be coupled with the tool assembly 108 in any suitable manner such as with threads as shown in FIG. 3.

FIG. 3 shows that in the illustrated embodiment, the elongate tubular body 148 has a distal portion 160, a proximal portion 164, and a lumen 168 that extends therethrough. The lumen 168 can have a distal portion that extends through a distal tubular member 172 and a proximal portion that extends at least partially through a proximal tubular member 176. The lumen 168 also extends through the indicator assembly 152, e.g., through a housing 200 thereof as discussed further below.

The drill 112 is configured to engage the proximal portion 164 of the elongate tubular body 148 and thereby to rotate the elongate tubular body 148. FIG. 3 shows a drive component 180 coupled with a proximal end of the proximal tubular member 176. The drive component 180 can have any suitable configuration for being engaged by the drill 112. For example the drive component can have a plurality of flat surfaces 182 to be engaged by a chuck of the drill 112. In the illustrated embodiment, the drive component 180 includes a small lumen 184 disposed therethrough. The lumen 184 is configured to be large enough to receive the guide pin 104. In various embodiments the elongate tubular body 148 is longer than the guide pin 104 such that when the elongate tubular body 148 is disposed over the guide pin 104 the proximal end 128 of guide pin 104 does not extend to or proximally of the drive component 180. The drive component 180 can be coupled with or can form a unitary extension of the proximal end of the proximal tubular member 176. In one embodiment a distal portion of the drive component 180 can be enlarged to have a recess (not shown) large enough to receive a proximal end of the proximal tubular member 176. The distal portion of the drive component 180 and the proximal portion of the proximal tubular member 176 can be joined in any suitable manner. For example, these components can be of unitary or monolithic construction or can be press fit together, welded, or joined by mechanical fasteners or an adhesive of any suitable type. FIG. 3 shows that the drive component 180 can have a stepped down profile along its length.

As noted herein, the drill 112 is used to rotate the tubular body 148 to cause the implement 144 to act on the bone or on an implant. If this procedure is performed through tissue, e.g., in a minimally invasive procedure with small incisions, it may be desirable to protect the tissue from the rotating tubular body 148. In some embodiments a protector 194 is provided along at least a portion of the elongate body 148, e.g., covering at least a portion of the distal tubular member 172. The protector 194 can be in the form of a bushing or other sleeve configured to enable relative motion of the portion of the elongate body 148 disposed therein, e.g., of the distal tubular member 172. FIG. 2B suggests that the sleeve need not completely encircle a spaced that receives the distal tubular member 172. Rather, the protector can cover a portion of the distal tubular member 172 sufficient to keep the tissue away from the rotating portions of the elongate tubular body 148. In one embodiment, the protector 194A has a circumferential gap 195A that extends along its length. The circumferential gap 195A enables the protector 174 to be easily assembled onto the distal tubular member 172. In one embodiment, the protector 194A is configured to be flexible enough to permit the circumferential gap 195A to expand to allow the distal tubular body 172 to pass through the circumferential gap 195A of the protector 174. The protector 194A preferably thereafter elastically returns toward the unexpanded state such that the distal tubular body 172 is securely retained in the protector 174. The circumferential gap 193A of the protector 194A enables the protector 174 to be removed from the distal tubular body 172, e.g., for cleaning. In other embodiments the protector 194 is cylindrical. Removal of the protector 194 is possible for example when the implement 144 is unthreaded and removed. Thereafter the protector 194 can be slid off the distal end of the distal tubular member 172. The protector 194 includes a plurality of apertures 195 that are useful for cleaning the protector 174.

In one embodiment, the tool assembly 108 is configured to restrict the axial movement of the protector 194. For example, a collar 196 can be provided in some embodiments that has a proximally facing shoulder 198. The proximally facing shoulder 198 preferably has a lateral dimension measured radially away from the outer surface of the distal tubular member 172 that is large enough to restrict motion of the protector 194. For example the shoulder 198 can have a lateral dimension measured radially away from the outer surface of the distal tubular member 172 that is greater than the thickness of the protector 194. The collar 196 and shoulder 198 are proximal extension of the implement 144 in the illustrated embodiment. In other embodiments, the collar is affixed to the distal tubular member 172 and can be left in place when the implement 144 is removed. The shoulder 199 limits distal movement of the protector 194 over the distal tubular member 172. In one embodiment, the protector 194 is disposed between opposing shoulders. For example, a distally facing shoulder 199 can be provided on a distal end of the indicator assembly 152. The distally facing shoulder 199 preferably has a lateral dimension measured radially away from the outer surface of the distal tubular member 172 that is large enough to restrict motion of the protector 194. For example the shoulder 199 can have a lateral dimension measured radially away from the outer surface of the distal tubular member 172 that is greater than the thickness of the protector 194.

Figure 7:
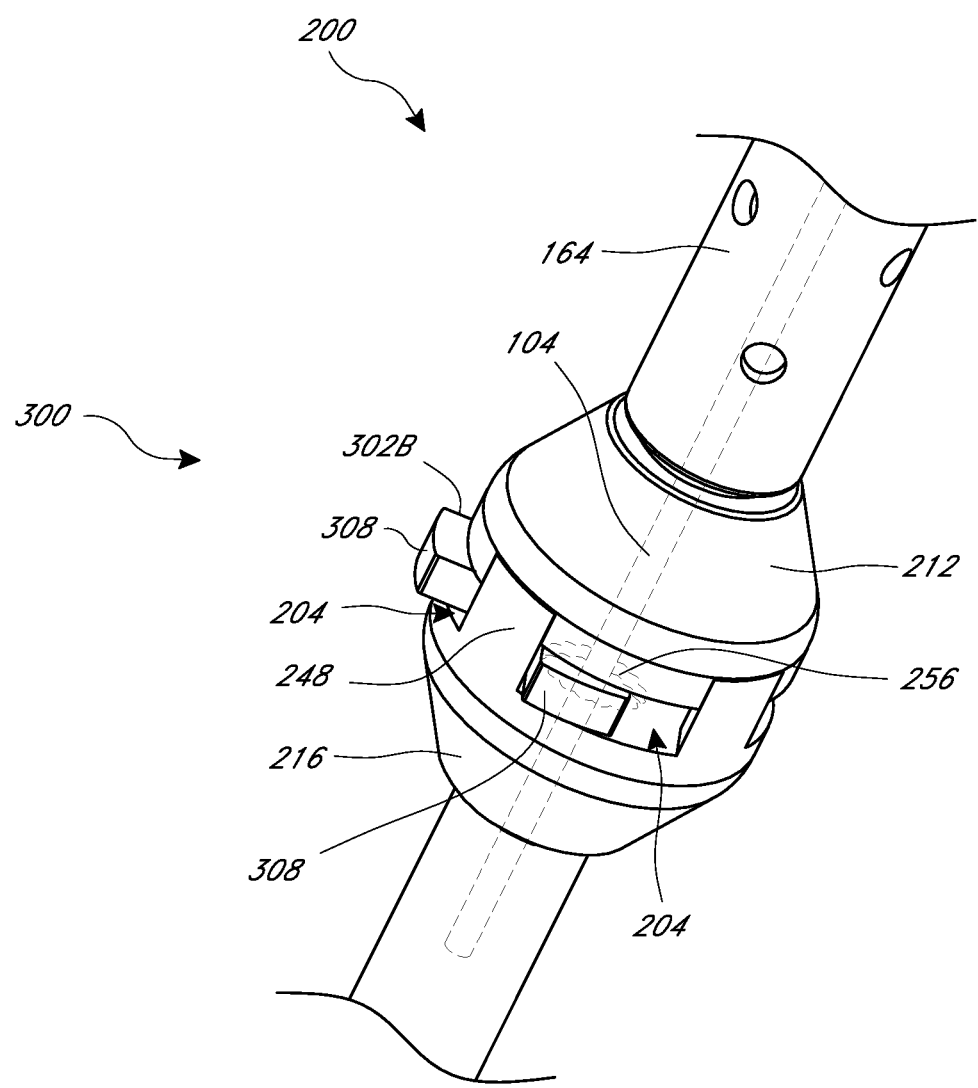
FIG. 7 is a perspective detail partial phantom view of one embodiment of an orthopedic driver, showing a mechanical alignment indicator with two modes of alignment feedback.

FIG. 3 shows the indicator assembly 152 being disposed between the proximal portion 164 and the distal portion 160 of the elongate tubular body 148. FIG. 7 shows that the indicator assembly 152 has a housing 200 having a plurality of lateral openings 204. In the illustrated embodiment, there are four openings 204 disposed symmetrically about the housing 200. The openings 204 can be disposed such that the circumferential mid-point of one of the openings 204 is 90 degrees apart from the circumferential mid-point of one of the openings 204, when viewed in a plane perpendicular to a longitudinal axis of the tool assembly 108. The lateral openings 204 are defined between a distal portion 212 of the housing 200 and a proximal portion 216 of the housing 200. The lateral openings 204 can be defined between a circumferential gap (discussed below) provided in a side surface of the proximal portion 216. In the illustrated embodiment, a proximal end of the proximal portion 216 is configured to receive a distal end of the proximal tubular member 176. In the illustrated embodiment, a distal end of the distal portion 212 is configured to receive a proximal end of the distal tubular member 172.

Figure 4A:
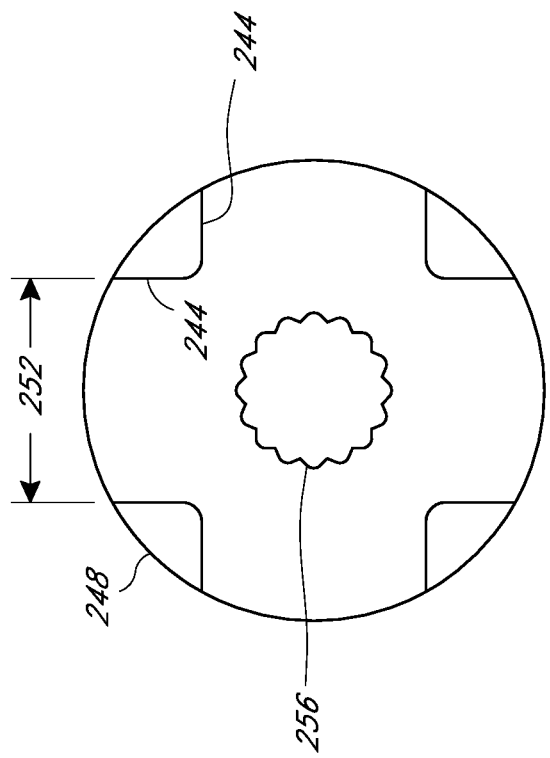
FIG. 4A is a plan view showing a non-smooth surface configured to create an audible sound from and/or vibrations in an orthopedic driver upon certain degrees of misalignment.
Figure 4:
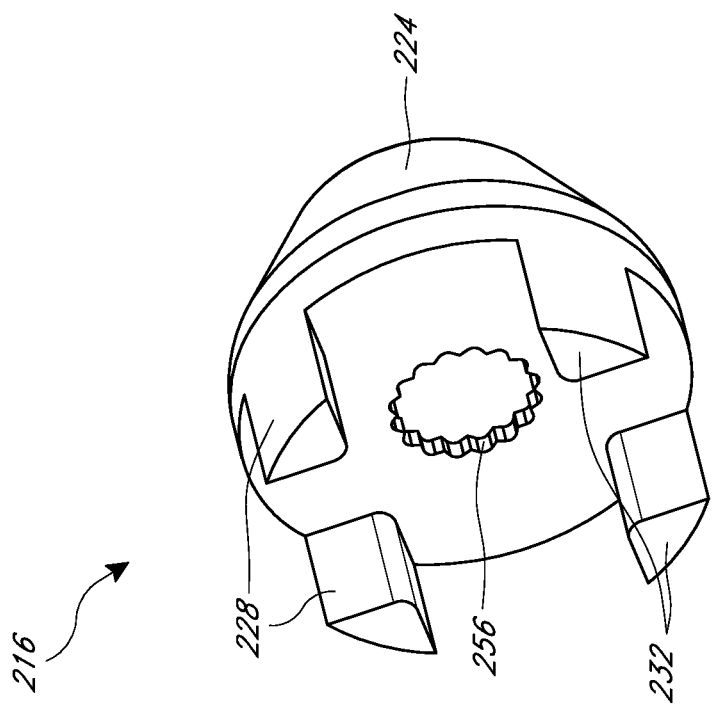
FIG. 4 is a perspective view of a portion of a housing for a mechanical alignment indicator.

FIGS. 4 and 4A show details of the proximal portion 216 of the housing 200. The proximal portion 216 includes a proximal body 224 and a plurality of distal posts 228. The distal posts 228 extend distally from a distal end of the proximal body 224. In the illustrated embodiment, the proximal body 224 has a tapered configuration. The tapered configuration provides a narrower profile at a proximal end of the body 224 and a wider profile at the distal end of the proximal body 224. Each of the distal posts 228 forms one circumferential edge of one of the openings 204. A distal end 232 of each of the distal posts 228 is adapted to be received in a corresponding structure of the distal portion 212 of the housing 200. Each of the distal posts 228 forms a portion of a cylindrical lateral surface of the indicator assembly 152. FIG. 4A shows that each of the distal posts 228 can be configured with a generally triangular cross-section, such as with two side surfaces 244 extending from a cylindrical outer surface 248. Two of the distal posts 228 in part define one of the openings 204 (shown in FIG. 7). In particular, two side surfaces 244 that face each other define a gap 252 therebetween. The gap 252 is provided in the lateral surface of the proximal portion 216. The gap 252 is one dimension, e.g., a circumferential dimension, of each of the openings 204. A dimension transverse to the gap 252 extends between a distal portion of the proximal body 224 and a proximal portion of the distal portion 212, as discussed further below. The gap 252 provides a space in which an indicator (discussed below) can move to indicate an aligned condition or to indicate a misalignment condition. In some embodiments, an indicator can slide radially in at least two directions in the gap 252 (e.g., left and right or up and down in FIG. 4A).

FIGS. 4 and 4A show that in one embodiment a non-smooth surface 256 is provided in the indicator housing 152. In particular, the non-smooth surface 256 can be disposed on the distal end of the proximal body 224. The non-smooth surface 256 can take any suitable form, for example can include a plurality of scallops, sinusoidal undulations, or other periodic or non-periodic deviations from a radius of curvature centered on a central axis of the lumen 168 when disposed in the tool assembly 108. As discussed in greater detail below, interaction between the guide pin 104 and the non-smooth surface 256 can provide a mechanical alignment indicator for indicating the alignment of the longitudinal axes of elongate body 148 and the guide pin 104. More particularly, direct contact between the non-smooth surface 256 and the guide pin 104 can result in the emission of audible sound from the tool assembly 108 upon rotational movement of the non-smooth surface 256 relative to the guide pin 104. Direct contact between the non-smooth surface 256 and the guide pin 104 can result in vibration in the tool assembly 108 upon rotational movement of the non-smooth surface 256 relative to the guide pin 104. Direct contact between the non-smooth surface 256 and the guide pin 104 can result in both the emission of audible sound from the tool assembly 108 and in vibration in the tool assembly 108 upon rotational movement of the non-smooth surface 256 to the guide pin 104. The guide pin 104 and the non-smooth surface 256 when interacting to produce an audible sound provide one means for indicating misalignment. The guide pin 104 and the non-smooth surface 256, when interacting to produce a vibration, provide another means for indicating misalignment. The guide pin 104 and the non-smooth surface 256, when interacting to produce a vibration and an audible sound, provide another means for indicating misalignment.

Figure 5:
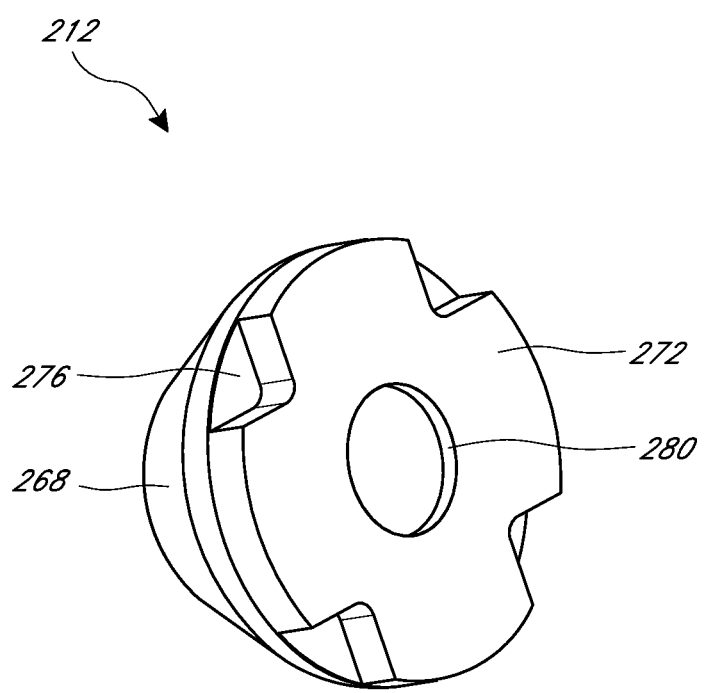
FIG. 5 is a perspective view of another portion of a housing for a mechanical alignment indicator.

FIGS. 3 and 5 show additional details of the distal portion 212 of the housing 200 of the indicator assembly 152. The distal portion 212 includes a distal body 268 and a proximal indicator support platform 272 coupled with the distal body 268. The proximal indicator support platform 272 can be integrally formed with the distal body 268 or can be attached thereto. The proximal indicator support platform 272 extends proximally of the proximal end of the distal body 268. A plurality of recesses 276 is provided, disposed about the indicator support platform 272. The recesses 276 are configured to receive the distal support posts 228. It is contemplated that various shaped recesses and correspondingly shaped distal ends are within the scope of this disclosure. Each of the recesses 276 may end in a triangular surface configured to receive one of the distal ends 232 of the distal posts 228. The illustrated embodiment, recesses 276 extending to four triangular surfaces are provided. An aperture 280 is provided through the distal body 268 and through indicator support platform 272. The aperture 280 is larger than the guide pin 104 such that some amount of movement of the guide pin within the aperture 280 is permitted. The length of the distal posts 228 of the proximal portion 216 and the depth of the recesses 276 extending from the triangular surfaces (or alternatively the height of the indicator support platform 272) are such that the openings 204 have sufficient height to permit an indicator (discussed below) to be slidably disposed between the distal and proximal portions 212, 216 of the indicator assembly 152.

Figure 6:
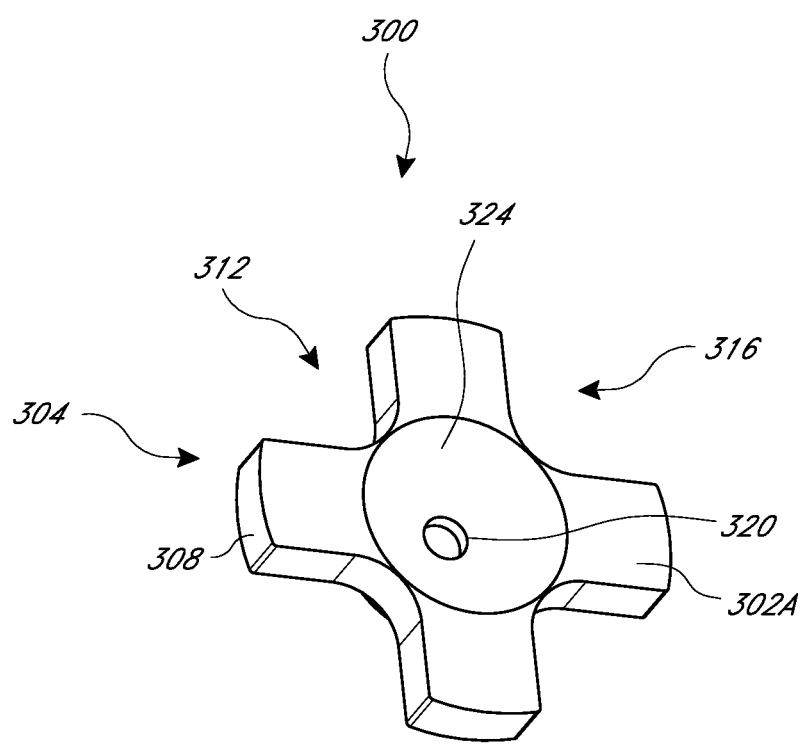
FIG. 6 is a perspective view of one embodiment of a visual indicator, which is one form of a mechanical alignment indicator.
Figure 11B:
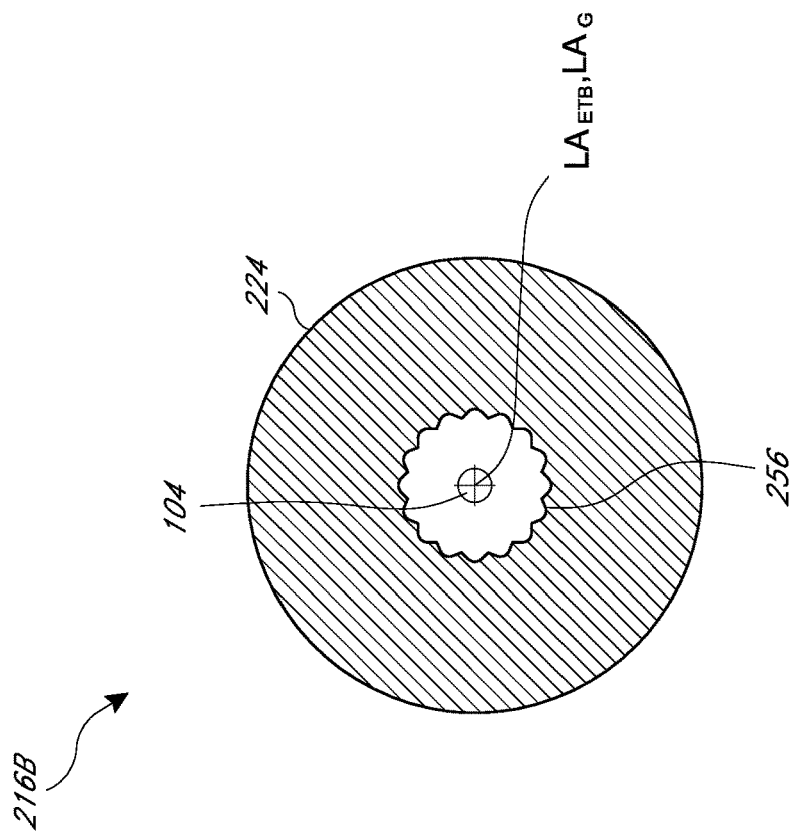
FIG. 11B is a top cross-section view of another embodiment of an orthopedic driver, showing an auditory or tactile indicator indicating a condition of misalignment in a condition of alignment.
Figure 11A:
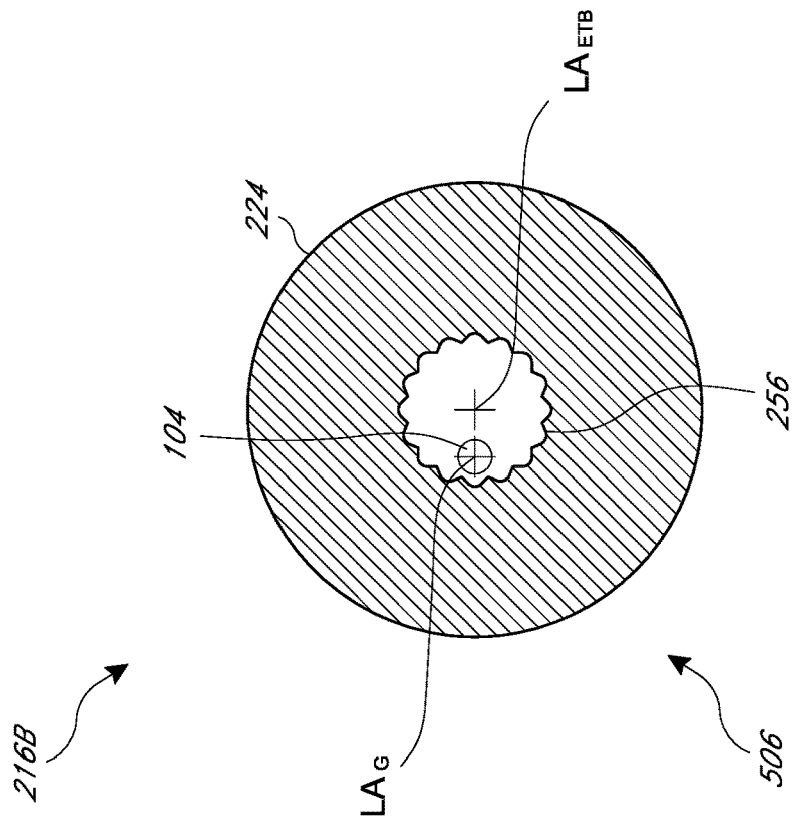
FIG. 11A is a top cross-section view of another embodiment of an orthopedic driver, showing an auditory or tactile indicator indicating a condition of misalignment in a condition of misalignment.

FIGS. 1-3 show that the indicator assembly 152 has an indicator 300 disposed therein. The indicator 300 can comprise any suitable form for being recessed in the housing 200 in one configuration of the tool assembly 108 and being extended therefrom in another configuration of the tool assembly 108. In one embodiment, illustrated in FIGS. 6-7, the indicator 300 has a disc structure having a distal face 302A and a proximal face 302B. The indicator 300 can include a plurality of radially extending arms 304. FIGS. 2 and 2A show that the arms 304 can be disposed 90 degrees apart when viewed in a plane perpendicular to a longitudinal axis of the tool assembly 108. That is, a central longitudinal axis of one of the arms 304 can be disposed 90 degrees from the central longitudinal axis of two adjacent arms 304 when viewed in a plane perpendicular to a longitudinal axis of the tool assembly 108. FIGS. 6 and 7 show that each of the plurality of radially extending arms 304 has an outer end 308. Each of the outer ends 308 is slidably disposed in a corresponding lateral opening 204 of the housing 200 in one configuration. In the illustrated embodiment, there are four arms 304 and four openings 204. In other embodiments, there can be more than four arms 304, e.g., five, six, seven, eight or more arms 304. In another embodiment, there can be fewer than four arms 304, e.g., one, two or three arms. FIGS. 11A and 11B illustrate embodiments in which a mechanical indication of alignment or misalignment is provided in which there are no arms or openings. An inner portion 312 of each of the arms 304 is coupled with an inner portion 316 of the indicator 300.

The inner portion 316 of the indicator 300 is configured to be disposed about, and in close contact with, a side surface of the guide pin 104. The inner portion 316 can include an aperture 320 that is slightly larger than the outer diameter of the guide pin 104. In one embodiment, the distal face 302A includes a structure to facilitate loading the tool assembly 108 over the guide pin 104. Such structure is useful where the aperture 320 has a diameter that is close in size to the diameter of the guide pin 104. The distal face 302A can include a concave surface 324 disposed between the inner portions 312 of the arms 204 and the aperture 320. The concave surface 324 can be centered on the aperture 320. The concave surface 324 can direct the guide pin 104 through the aperture 320. Because the indicator 300 is movable in the housing 200 the concave surface 324 can also cause the aperture 320 of the indictor to translate to a position closer to the central longitudinal axis of the elongate tubular body $LA_{ETB}$. The concave surface 324 can take any suitable form. For example, the concave surface 324 can be at least partially conical in one embodiment.

The indicator 300 is rotatable with the elongate tubular body 148 about the guide pin 104. FIG. 2A shows that the distal posts 228 of the proximal portion 216 of the indicator assembly 152 are in the same plane as the body of the indicator 300. More particularly, a plane disposed transverse to the longitudinal axis of the tool assembly 108 includes a portion of each of the arms 204 and a portion of each of the posts 228. The posts 228 are rigidly connected to other portions of the elongate body 148. When the elongate body 148 is rotated by the drill 112, the posts 228 are also rotated. The indicator 300 is movable between the posts 228, but side surfaces of the posts 228 push the indicator 300 in rotation. Thus, rotation of the drill 112 rotates the tool assembly 108 including the elongate tubular body 148, the housing 200, and the indicator 300. While the indicator 300 rotates with the distal and proximal portions 212, 216 of the housing 200 relative motion of the indicator and the housing 200 is generally limited to sliding in a lateral direction or in a radial direction on the platform 272 and within and out of the openings 204.

The indicator 300 is supported in the housing 200 such that a change in the lateral position of the elongate tubular body 148 relative to the guide pin 104 causes the outer ends 308 of the radially extending arms 304 of the indicator 300 to move. FIG. 7 shows that such movement can dispose the outer end 308 of one of the arms 304 at a position laterally or radially outward of a lateral surface of the housing 200. FIG. 7 shows that such movement can dispose the outer end 308 of one of the arms 304 at a position laterally or radially outward of the cylindrical outer surfaces 248 of the posts 212.

Figure 8B:
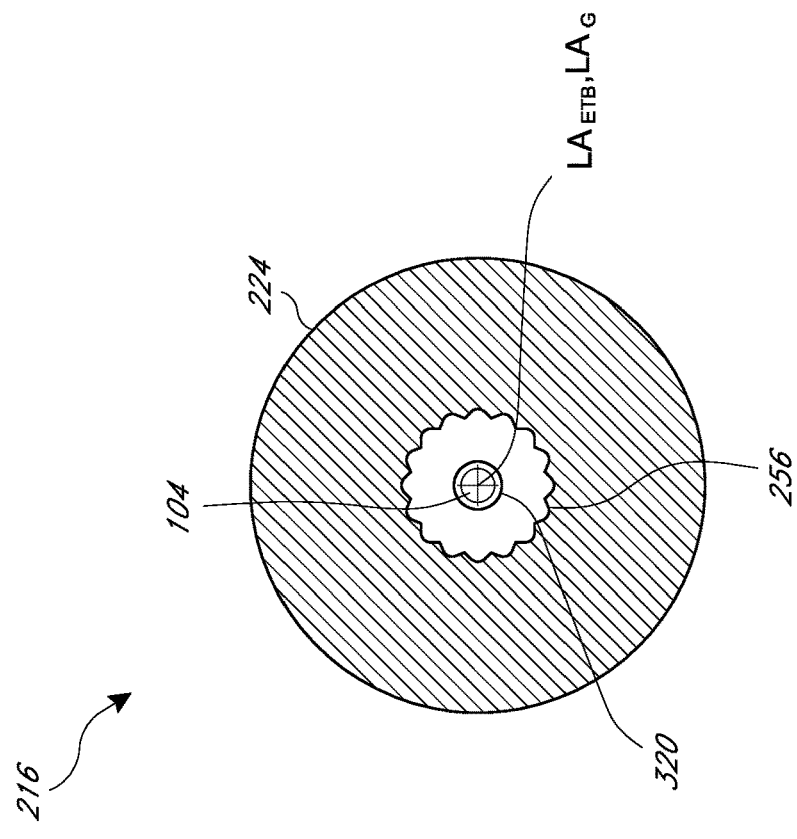
FIG. 8B is a top cross-section view of the orthopedic driver of FIG. 7 showing a condition of alignment.
Figure 8A:
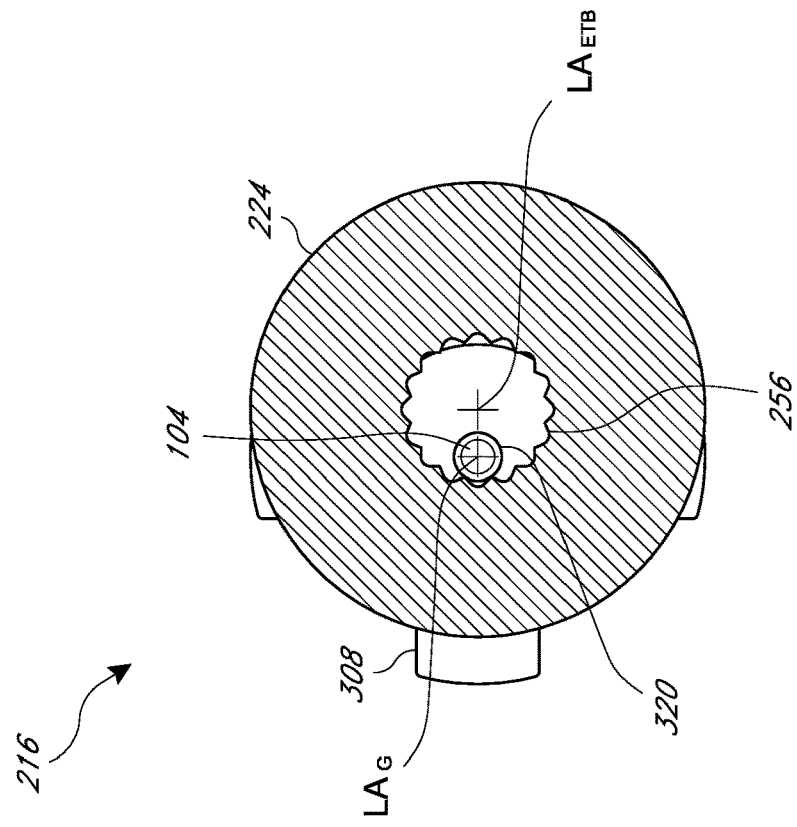
FIG. 8A is a top cross-section view of the orthopedic driver of FIG. 7 showing a condition of misalignment.
Figure 9:
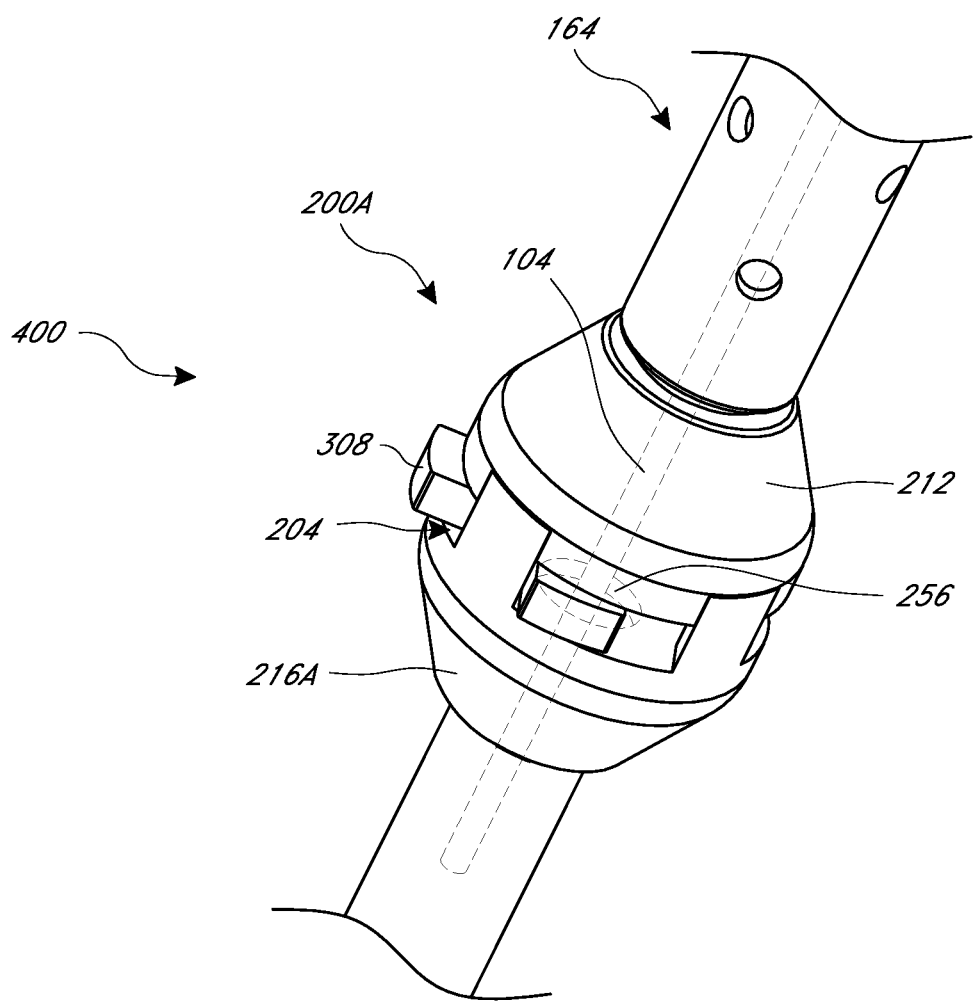
FIG. 9 is a perspective detail partial phantom view of another embodiment of an orthopedic driver, showing a visual indicator indicating a condition of misalignment.
Figure 10A:
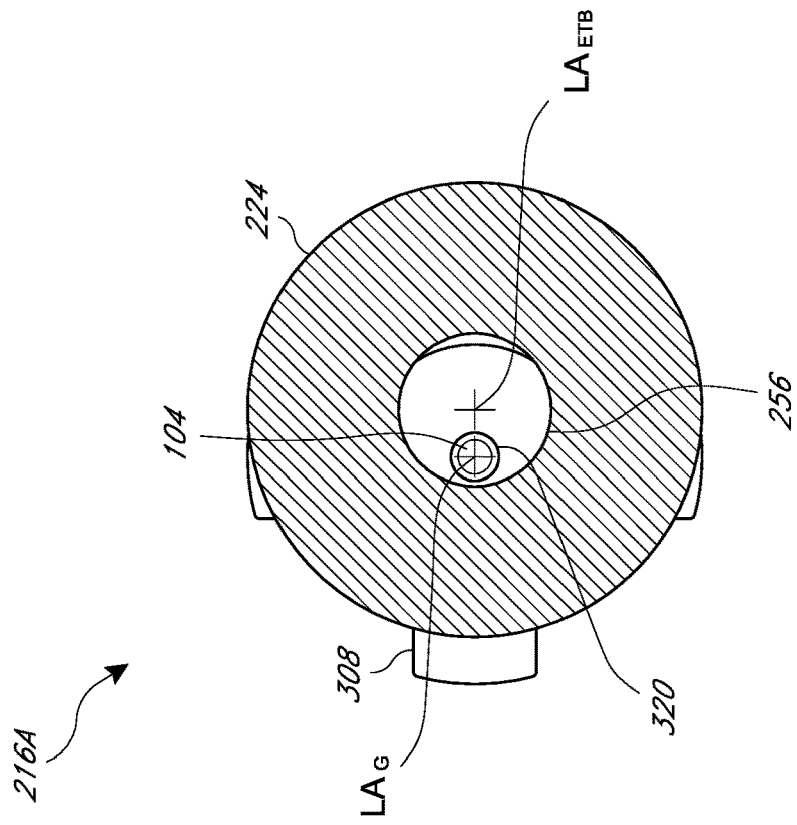
FIG. 10A is a top cross-section view of the orthopedic driver of FIG. 9 showing a condition of misalignment.

FIGS. 8A and 10A show that in various embodiments, the visual indicator 300 is coupled with the guide pin 104 such that relative lateral movement of the elongate tubular body relative to the guide pin 104 causes the visual indicator 300 to move between a flush or recessed configuration within the housing 200 (FIGS. 2A, 8B and 10B) and an extended configuration in which the visual indicator extends outward of the housing (FIGS. 7, 8A, 9 and 10A). The flush or recessed configuration corresponds to alignment of the guide pin 104 relative to the elongate tubular body 148 and the extended configuration corresponds to misalignment of the guide pin 104 relative to the elongate tubular body 148. The indicator 300 thus provides a means for indicating misalignment.

FIG. 7 shows that one of the arms 304 has a length sufficient to extend through a corresponding opening 204 to a position laterally outward of a lateral surface of the housing, e.g., to a position lateral of the cylindrical outer surface 248. The flush configuration of FIG. 2A is provided in part from the width of the indictor 300 being less than or equal to the diameter of the housing 200. For example, a distance provided between the outer ends 308 of two arms disposed 180 degrees apart is less than or equal to the width of the housing 200 adjacent to the openings 204. In this context, the distance is measured as a line extending parallel to or in a plane containing the longitudinal axes of the arms 304 and the center of the aperture 320. Where the distance is less than the diameter of the housing 200 adjacent to the openings 204, the ends 308 can be recessed in the openings 204. To enable the indicator 300 to be visible, the lateral movement of the indicator 300 greater than the distance that the ends 308 are recessed is provided. One approach to providing sufficient lateral movement is to make the lateral dimension of the arms 304 smaller than the width of the openings, i.e., the gap 252. For example, the dimension of the arms 304 perpendicular to the longitudinal axis of the arms can be about ¾ the dimension of the gap 252. To provide more lateral movement, the dimension of the arms 304 perpendicular to the longitudinal axis of the arms can be about ½ the dimension of the gap 252. To provide still more lateral movement, the dimension of the arms 304 perpendicular to the longitudinal axis of the arms can be about ¼ the dimension of the gap 252.

The indicator 300 rotates with the tool assembly 108 in one mode or phase of operation. When one of the ends 308 extends through and out of an opening 204 and the tool assembly 108 is rotating the protrusion is visible as an eccentric blur. This blur in rotation corresponds to the relative position of a longitudinal axis $LA_G$ and the guide pin and the longitudinal axis of the elongate tubular body $LA_{ETB}$ as shown in FIG. 8A. The eccentric blur is immediately visible to the user. Because it is immediately visible, the user can quickly re-position the tool assembly 108 to reduce, e.g., to minimize, the time that the tool 108 is rotating off-set from the guide pin 104. Keeping the eccentric blur to a minimum or retaining the tool assembly 108 in the recessed configuration is one way to retain the longitudinal axis $LA_G$ and the guide pin and the longitudinal axis of the elongate tubular body $LA_{ETB}$ substantially parallel to, e.g., coincident with, each other as shown in FIG. 8B.

In another mode or phase of operation the indicator 300 can indicate misalignment when the tool assembly 108 is not rotating. As discussed above, the guide pin 104 extends through the aperture 320. As the longitudinal axis $LA_G$ and the guide pin and the longitudinal axis of the elongate tubular body $LA_{ETB}$ become misaligned one or more of the ends 308 emerges from one or more of the openings 204. Thus, even prior to rotation the user can see whether the axes $LA_G$, $LA_{ETB}$ are generally aligned or may be misaligned. This is an important way to avoid initial errors in the initial direction of advance of the implement 144 before the tool assembly 108 begins to act on the bone or an implant to be positioned in the bone.

Figure 10B:
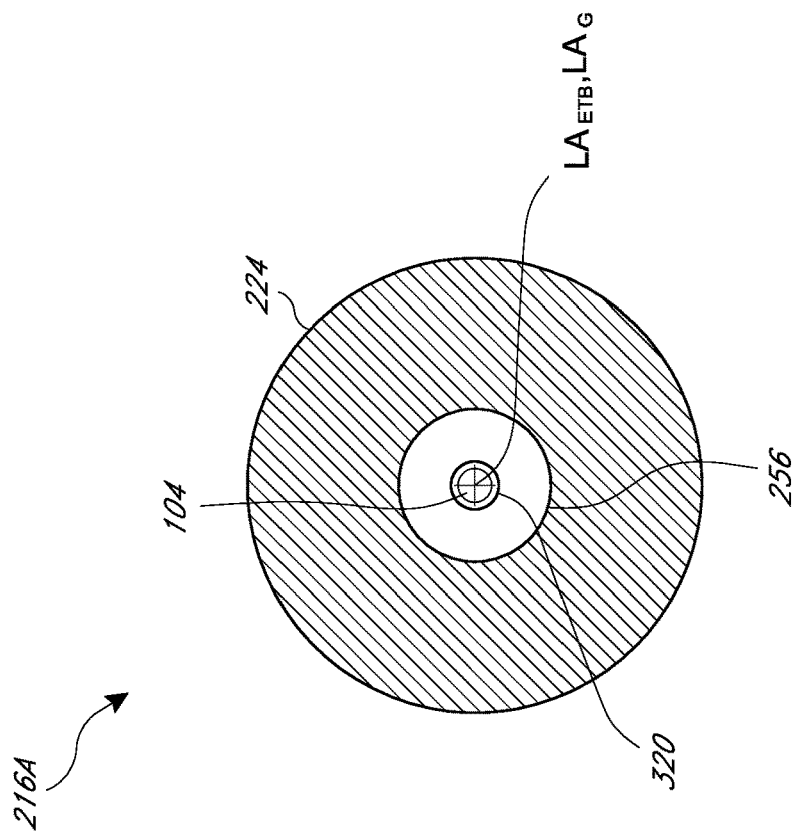
FIG. 10B is a top cross-section view of the orthopedic driver of FIG. 9 showing a condition of alignment.

FIGS. 9-10B illustrate an embodiment of an orthopedic driver 400 having an indicator 300 that provides visual indication of alignment without requiring audible and/or vibratory tactile feedback. The indicator 300 is disposed in a housing that has a smooth surface 256A disposed about an interior lumen 424. The smooth surface 256A can be disposed on one or both of proximal and distal portions of a housing 200A. In the illustrated embodiment, the distal end of a proximal body 224A of a proximal portion 216A of the housing 200A includes the smooth surface 256A. The indicator 300 provides alignment feedback by displacement of the end 308 out of an opening 204 as shown in FIG. 10B and similar to the embodiment discussed above. As discussed above, the indicator 300 rotates with elongate tubular body 148. In an out of alignment configuration the end 308 is displaced out of the housing 200A (when rotating or when not rotating relative to the guide pin 104). In this position the longitudinal axis $LA_G$ and the guide pin and the longitudinal axis of the elongate tubular body $LA_{ETB}$ are off-set. The smooth surface 256A may directly contact the guide pin 104 without substantial audible sound or vibration due to the smoothness of the surface.

FIGS. 11A and 11B illustrate another embodiment in which an indicator assembly 506 is provided. The indicator assembly 506 includes a mechanical alignment indicator by incorporating the non-smooth surface 256 into a proximal housing 216B. The proximal housing 216B forms part of a housing similar to the housing 200 described above. The non-smooth surface 256 is capable of contacting the guide pin 104 as indicated in FIG. 11A when there is misalignment between the longitudinal axis $LA_G$ and the guide pin 104 and the longitudinal axis $LA_{ETB}$ of an elongate tubular body including the proximal housing 216B. Such contact produces one or both of an audible sound or a vibration in the tool assembly in which the non-smooth surface 256 is disposed. The sound or vibration provides mechanical feedback to the user to reposition the tool assembly including the non-smooth surface 256 (e.g., in the proximal housing 216B) relative to the guide pin 104. Such repositioning can cause the longitudinal axis $LA_G$ and the guide pin 104 and the longitudinal axis $LA_{ETB}$ of an elongate tubular body into which the housing 216B is incorporated to be aligned as in FIG. 11B.

FIGS. 1 and 7-11B illustrate various methods in connection with the tools discussed herein. As discussed above, a guide pin 104 can be placed into the bone B to a depth sufficient to secure the guide pin in the bone and at a desired alignment angle relative to the bone. The tool assembly 108 is then positioned over the guide pin 104. The elongate tubular body 148 is positioned over a proximal portion of the guide pin 104. The elongate tubular body 148 has a mechanical alignment feedback indicator disposed therein. In the embodiment of FIGS. 9-10B the mechanical alignment feedback indicator includes a visible or visual indicator as discussed above. In the embodiment of FIGS. 11A-11B the mechanical alignment feedback indicator includes a non-smooth surface 256 that provides audible or tactile feedback upon direct contact between the non-smooth surface and the guide pin 104. In the embodiment of FIGS. 1-8B, the mechanical alignment feedback indicator includes both the non-smooth surface 256 and the visible or visual indicator 300 such that more feedback can be provided.

In the case of the embodiment of FIGS. 1-7, the indicator 300 is activated upon misalignment of the elongate tubular body 148 of the tool assembly 108 and the guide pin 104. Such feedback can be provided when there is relative rotation between the tool assembly 104 and the guide pin 104 or when there is no such relative rotation. FIG. 8A shows that the mechanical alignment indicator is activated by the guide pin 104 directly pushing the indicator 300 such that the outer end 308 of one of the arms 304 emerge from the openings 204 in the housing 200 and is visible. As noted above when the ends emerge from the openings 204 and the tool 108 is rotated, a blur pattern is visible.

FIG. 8A shows that the mechanical alignment indicator is activated by the guide pin 104 coming into direct contact with the non-smooth surface 256. Relative rotation causes periodic contact between the guide pin 104 and the non-smooth surface 256. If the non-smooth surface 256 comprises a plurality of equally spaced scallops the mechanical alignment indicator may produce a repeating audible sound that is different from the sound of the drill or other operating room components. This repeating sound can be a staccato chattering sound. This structure can be configured to induce a vibration in the tool assembly 108 that is felt by the user. Thus, vibration is another mechanical alignment indicator that can provide feedback to the user.

In one method, the user repositions the elongate body 148 of the tool assembly 108 in response to feedback. The repositioning can be during relative rotation between the tool assembly 108 and the guide pin 104 or when there is no such relative rotation, e.g., before any rotation has taken place. The feedback can include at least one of an extension of a portion of the visual indicator 300 from a side surface of the housing 200. The feedback can include an emission of an audible sound arising from direct contact between the non-smooth surface 256 and the guide pin 140. The feedback can include a vibration in the elongate tubular body 148 of the tool assembly 108 arising from direct contact between the non-smooth surface 356 (or other mechanical alignment indicator) and the guide pin 140. The repositioning of the elongate body 148 causes the longitudinal axis $LA_G$ of the guide pin 104 and the longitudinal axis $LA_{ETB}$ of the elongated tubular body 148 to be moved back toward alignment, e.g., with these axis coincident as shown in FIG. 8B.

Various configurations provide feedback to maintain alignment of the tool assembly 108 and the guide pin 104. Alignment includes where the longitudinal axis $LA_G$ of the guide pin 104 and the longitudinal axis $LA_{ETB}$ of the elongated tubular body 148 are perfectly aligned. In various embodiments, misalignment triggering feedback can include a condition where the axes $LA_G$, $LA_{ETB}$ are at least partially offset, e.g., non-parallel. The axes $LA_G$, $LA_{ETB}$ can be offset when they cross at the surface of the bone but are not co-linear at the location of the housing 200. In some embodiments, feedback is not triggered at small offsets of the axes $LA_G$, $LA_{ETB}$. For example, a threshold angle can be provided below which feedback is not provided and above which feedback is provided. In some embodiments, the threshold angle is between about 0.5 degrees and about 10 degrees. In other embodiments, the threshold angle is between about 1 degree and about 5 degrees. In other embodiments, the threshold angle is between about 0.5 degree and about 4 degrees. In other embodiments, the threshold angle is between about 0.5 degree and about 3 degrees. In other embodiments, the threshold angle is between about 0.5 degree and about 2 degrees. In embodiments, threshold angle may vary depending on relationship of cannula size/diameter to the guide pin size/diameter.

In some embodiments, feedback may be of more than one type and more than one threshold angle is provided. For example, a first threshold can be provided in which a lower level of misalignment is provided between the axes $LA_G$, $LA_{ETB}$. A first feedback corresponding to misalignment exceeding the first threshold offset between the axes $LA_G$, $LA_{ETB}$ can include visual feedback provided by the arms 304 emerging from the openings 204 as discussed above. The first feedback can arise at a lower level of misalignment, e.g., at above about 0.5 degrees. A second feedback corresponding to misalignment exceeding a second threshold offset between the axes $LA_G$, $LA_{ETB}$ can be provided and can include audible and/or tactile feedback. The audible and/or tactile feedback can be provided by direct contact between the guide pin 104 and the non-smooth surface 256. The second feedback can arise at a higher level of misalignment, e.g., at above about 1 degree or about above 5 degrees. In various embodiments, the first and second feedback will be present simultaneously when the second threshold is exceeded.

The methods illustrated by FIGS. 10A and 10B are similar to those of FIGS. 8A and 8B. FIG. 10A shows misalignment of the longitudinal axis $LA_G$ of the guide pin 104 and the longitudinal axis $LA_{ETB}$ of the elongated tubular body including the proximal housing 216A. Although there may be contact between the guide pin 104 and the smooth surface 256A, such contact will not result in noticeable vibration or audible sound. Rather, the extension of the end 308 of the arm 304 will provide visual feedback to reposition the system to a more aligned state, as in FIG. 10B. Such feedback can be provided when there is relative rotation between the tool assembly 108 and the guide pin 104 or when there is no such relative rotation.

The methods illustrated by FIGS. 11A and 11B are similar to those of FIGS. 8A and 8B. FIG. 11A shows misalignment of the longitudinal axis $LA_G$ of the guide pin 104 and the longitudinal axis $LA_{ETB}$ of the elongated tubular body including the proximal housing 216B. Contact between the guide pin 104 and the non-smooth, e.g., undulated surface 256 results in noticeable vibration or audible sound. There need not be any visible change in the appearance of the tool. The vibration or sound provides mechanical feedback to move the system to a more aligned state, as in FIG. 11B. The apparatuses and method illustrated by FIGS. 11A and 11B allow a mechanical indicator to be activated upon relative rotation between the tool assembly and the guide pin 104. These apparatuses and methods can eliminate the openings 204, providing a simpler and/or more enclosed arrangement.

The foregoing devices and methods can be used to achieve much improved control of steps of preparing bone in connection with orthopedic procedures. For example, the implement 144 can include a bone cutting or reaming implement. In some embodiments implement 144 may be comprised of a drill bit, a reamer, a broach, a rongeur, a rasp, a file, or other implements. Such implements can be used to prepare a surface to receive an implant or to cut recesses or channels in bones for other purposes. The implement 144 can be a tool interface configured to be coupled with an implant to enable the tool assembly 108 to drive the implant into bone. Thus, the implement 144 can be an implant driving interface.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A method comprising;
placing a distal portion of a guide pin in a bone;
positioning an elongate tubular driver over a proximal portion of the guide pin, the elongate tubular driver comprising a body having a mechanical alignment indicator disposed therein, the mechanical alignment indicator activated upon misalignment of the elongate tubular driver and guide pin; and
repositioning the elongate tubular driver in response to an extension of the mechanical alignment indicator from a side surface of the elongate tubular driver.

2. The method of claim 1, wherein the elongate tubular body is coupled with a bone cutting implement and further comprising reaming the bone over the guide pin.

3. The method of claim 2, wherein repositioning the elongate tubular driver occurs during reaming.

4. The method of claim 2, wherein repositioning the elongate tubular driver occurs when there is no reaming.

5. The method of claim 1, wherein the elongate tubular body is coupled with an implant and further comprising advancing the implant into the bone over the guide pin.

6. The method of claim 1, wherein the extension of the mechanical alignment indicator provides a visual indication of misalignment of the guide pin.

7. The method of claim 1, wherein the mechanical indicator comprises a plurality of radially extendable arms.

8. The method of claim 1, wherein repositioning the elongate tubular driver comprises moving the elongate tubular driver relative to the guide pin until the mechanical alignment indicator no longer extends from the side surface of the elongate tubular driver.

9. A method comprising;
placing a distal portion of a guide pin in a bone;
positioning an elongate tubular driver over a proximal portion of the guide pin, the elongate tubular driver comprising a body having a mechanical alignment indicator disposed therein, the mechanical alignment indicator activated upon misalignment of the elongate tubular driver and guide pin; and
repositioning the elongate tubular driver in response to an emission of an audible sound arising from direct contact between the mechanical alignment indicator and the guide pin.

10. The method of claim 9, wherein the elongate tubular body is coupled with a bone cutting implement and further comprising reaming the bone over the guide pin.

11. The method of claim 10, wherein repositioning the elongate tubular driver occurs during reaming.

12. The method of claim 10, wherein repositioning the elongate tubular driver occurs when there is no reaming.

13. The method of claim 9, wherein the elongate tubular body is coupled with an implant and further comprising advancing the implant into the bone over the guide pin.

14. A method comprising;
placing a distal portion of a guide pin in a bone;
positioning an elongate tubular driver over a proximal portion of the guide pin, the elongate tubular driver comprising a body having a mechanical alignment indicator disposed therein, the mechanical alignment indicator activated upon misalignment of the elongate tubular driver and guide pin; and repositioning the elongate tubular driver in response to a vibration in the elongate tubular driver arising from direct contact between the mechanical alignment indicator and the guide pin.

15. The method of claim 14, wherein the elongate tubular body is coupled with a bone cutting implement and further comprising reaming the bone over the guide pin.

16. The method of claim 15, wherein repositioning the elongate tubular driver occurs during reaming.

17. The method of claim 15, wherein repositioning the elongate tubular driver occurs when there is no reaming.

18. The method of claim 14, wherein the elongate tubular body is coupled with an implant and further comprising advancing the implant into the bone over the guide pin.

* * * * *